United States Patent
Klausman et al.

(10) Patent No.: US 11,759,239 B2
(45) Date of Patent: Sep. 19, 2023

(54) MIS MULTI-LEVEL COMPRESSOR / DISTRACTOR

(71) Applicant: Astura Medical Inc., Carlsbad, CA (US)

(72) Inventors: Keith Klausman, Carlsbad, CA (US); Thomas Purcell, Carlsbad, CA (US); Joel Gambrell, Carlsbad, CA (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 16/581,727

(22) Filed: Sep. 24, 2019

(65) Prior Publication Data

US 2020/0093517 A1    Mar. 26, 2020

Related U.S. Application Data

(60) Provisional application No. 62/735,824, filed on Sep. 24, 2018.

(51) Int. Cl.
A61B 17/70 (2006.01)
A61B 17/02 (2006.01)

(52) U.S. Cl.
CPC .......... *A61B 17/708* (2013.01); *A61B 17/025* (2013.01); *A61B 2017/0256* (2013.01)

(58) Field of Classification Search
CPC .......... A61B 17/7074–7092; A61B 2017/0256
See application file for complete search history.

(56) References Cited

U.S. PATENT DOCUMENTS

| | | | |
|---|---|---|---|
| 8,394,109 B2 * | 3/2013 | Hutton | A61B 17/7085 606/105 |
| 9,480,504 B1 * | 11/2016 | Schafer | A61B 17/708 |
| 9,907,582 B1 | 3/2018 | Olea | |
| 10,136,927 B1 * | 11/2018 | Lish | A61B 17/7083 |
| 2008/0077138 A1 * | 3/2008 | Cohen | A61B 17/708 606/86 A |
| 2008/0119862 A1 * | 5/2008 | Wicker | A61B 17/708 606/99 |
| 2008/0125788 A1 * | 5/2008 | Cohen | A61B 17/708 606/104 |
| 2008/0177270 A1 * | 7/2008 | Sorrenti | A61B 17/8605 606/90 |
| 2010/0004695 A1 * | 1/2010 | Stad | A61B 17/7074 606/86 A |
| 2011/0130793 A1 * | 6/2011 | Woolley | A61B 17/7076 606/279 |
| 2012/0271308 A1 | 10/2012 | Dominik | |
| 2013/0289633 A1 * | 10/2013 | Gleeson | A61B 17/708 606/86 A |
| 2014/0277198 A1 * | 9/2014 | Stad | A61B 17/7035 606/86 A |

(Continued)

OTHER PUBLICATIONS

Hternational Search Report and Written Opinion in PCT Application No. PCT/US2019/052 dated Nov. 15, 2019.

(Continued)

*Primary Examiner* — Eduardo C Robert
*Assistant Examiner* — Steven J Cotroneo
(74) *Attorney, Agent, or Firm* — Michael R Shevlin

(57) ABSTRACT

A multi-level compressor/distractor instrument that provides both linear and lordotic/kyphotic induced compression and distraction.

6 Claims, 7 Drawing Sheets

(56) References Cited

U.S. PATENT DOCUMENTS

| | | | |
|---|---|---|---|
| 2015/0066042 A1* | 3/2015 | Cummins | A61B 17/7091 |
| | | | 606/104 |
| 2015/0066088 A1* | 3/2015 | Brinkman | A61B 17/7077 |
| | | | 606/264 |
| 2015/0351814 A1 | 12/2015 | McClintock et al. | |
| 2016/0000468 A1 | 1/2016 | Samdani et al. | |
| 2017/0196597 A1* | 7/2017 | Corbin | A61B 17/025 |
| 2017/0311985 A1* | 11/2017 | Bobbitt | A61B 17/7002 |
| 2018/0214189 A1* | 8/2018 | Olea | A61B 17/7079 |
| 2018/0249992 A1* | 9/2018 | Truckey | A61B 17/0206 |
| 2019/0000437 A1 | 1/2019 | Dipoto et al. | |
| 2020/0054361 A1* | 2/2020 | Peultier | A61B 17/7085 |
| 2020/0107862 A1* | 4/2020 | Biedermann | A61B 17/7032 |

OTHER PUBLICATIONS

International Preliminary Report on Patentability in PCT Application No. PCT/US2019/052805 dated Apr. 16, 2020.

\* cited by examiner

MIS MULTI-LEVEL COMPRESSOR / DISTRACTOR

CROSS-REFERENCE TO RELATED APPLICATIONS

This application claims the benefit of U.S. Provisional Application No. 62/735,824 filed Sep. 24, 2018, which is incorporated herein by reference.

FIELD

The present invention relates generally to the field of surgery, and more specifically, to a multi-level compressor/distractor for use in spinal fusion surgery.

BACKGROUND

In many surgical spinal procedures pedicle screws are inserted into the vertebrae of the defective region and spinal fixation rods are used to rigidly fix the vertebrae relative to one another between the screws. Typically, screw extenders may attach to the screws and are used to assist with insertion of the spinal rods. In many cases, adjustment of the screws is needed to put the spine in the correct position for the spinal rod. This is usually done by applying compression and/or distraction forces of a compressor/distractor instrument to vertebrae via the screw extenders in the defective region.

In some cases, the defective region includes lordotic and/kyphotic curvature. The defective region may also include multiple levels of vertebrae. In some cases, one of the levels of the spine must be skipped during the compression and distraction procedures.

Current multi-level compressors/distractors only provide linear compression or distraction without the ability to manipulate lordosis at a targeted spinal segment.

Current multi-level compressors/distractors only provide lordosis/kyphosis generating compression or distraction without the ability to linearly compress or distract.

Current multi-level compressors/distractors do not have an internal threaded reduction feature that also provides bending support to the screw extender, tower or implant.

Current multi-level compressors/distractors which utilize a thread to produce mechanical advantage are an inconvenience to assemble to a spinal construct due to inefficiently manipulating the mechanism to achieve alignment.

Accordingly, there remains a need for instruments and methods that provide solutions to the problems of current systems. The present invention is directed toward meeting these needs.

SUMMARY

The present invention is directed to a minimally invasive surgery multi-level compressor/distractor instrument that provides both linear and lordotic/kyphotic induced compression and distraction. In some embodiments, the minimally invasive surgery multi-level compressor/distractor instrument decouples from its threaded mechanism to provide freedom during assembly to the spinal construct. In some embodiments, the minimally invasive surgery multi-level compressor/distractor instrument utilize support tubes as a two for one to provide strength to the tower or implant during compression or distractor manipulation and to also engage the set screw for reduction and tightening/loosening purposes. In some embodiments, the support tubes provide strength to the tower or implant internally where as other devices are external which requires a larger incision.

DETAILED DESCRIPTION

The present invention is directed to a MIS Multi-Level Compressor/Distractor provides both linear and lordotic/kyphotic induced compression and distraction where other devices only provide one or the other.

In some embodiments, the MIS Multi-Level Compressor/Distractor decouples from its threaded mechanism to provide freedom during assembly to the spinal construct.

In some embodiments, the MIS Multi-Level Compressor/Distractor utilizes Compressor/Distractor support tubes that provide two functions, the first is the compressor/distractor support tubes provide strength internally to screw extenders or towers during compression or distraction manipulation and to also engage the set screw for reduction and tightening/loosening purposes.

The MIS Multi-Level Compressor/Distractor support tubes provide strength to the screw extenders or tower internally where as other devices are external which requires a larger incision.

The MIS multi-level compressor/distractor with pre-assembled MIS compressor/distractor support tubes is a device which provides compression and distraction to targeted spinal segments. Compression and distraction is provided in a linear direction by way of a ratcheting rack and pinion. Compression and distraction is also achieved by inducing lordosis or kyphosis by way of two pivoting arms controlled by a threaded shaft. The multi-level compressor/distractor assembles to the spinal construct with ease by setting the ratchet on the slide to neutral which allows the slide to move freely. The two pivoting arms pivot freely by positioning the thread release cam down which decouples the pivot arm from the threaded shaft. The MIS compressor/distractor support tubes provide internal set screw engagement for threaded reduction capabilities while also providing bending support during compression or distraction manipulation. Threaded reduction is performed by engaging the MIS compressor/distractor support tubes at the proximal end with a driver.

Figure 1:
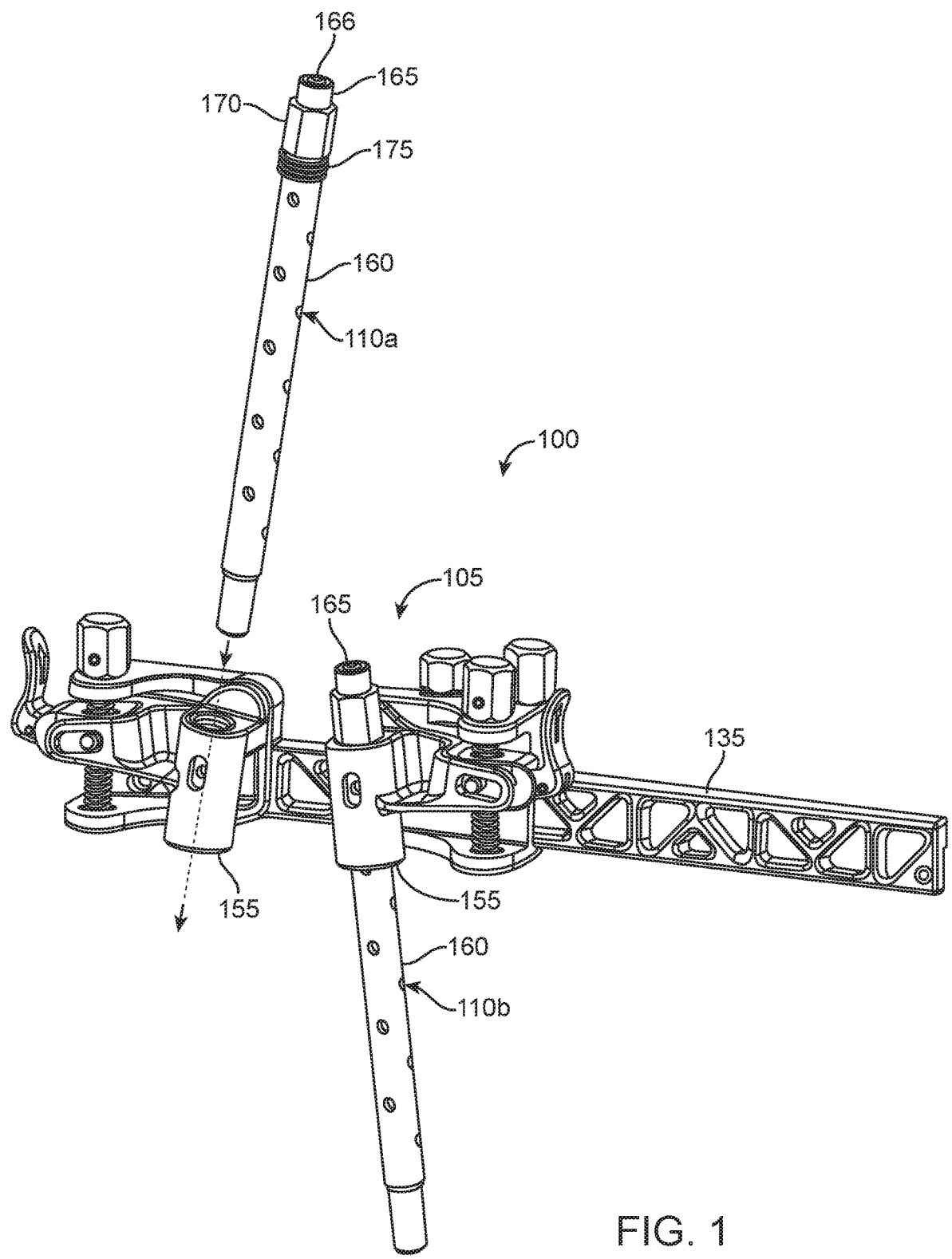
FIGS. 1 and 2 are perspective views showing ne embodiment of a minimally invasive surgery (MIS) multi-level compressor/distractor instrument.
Figure 2:
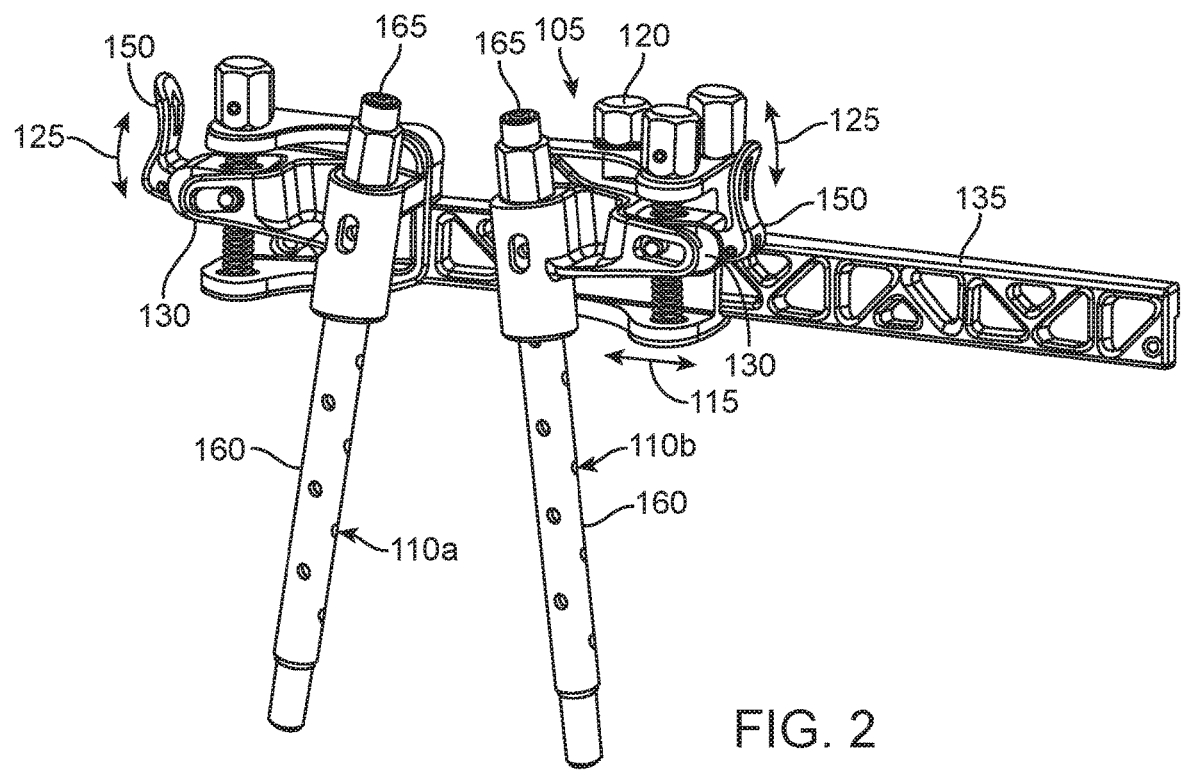
Figure 3:
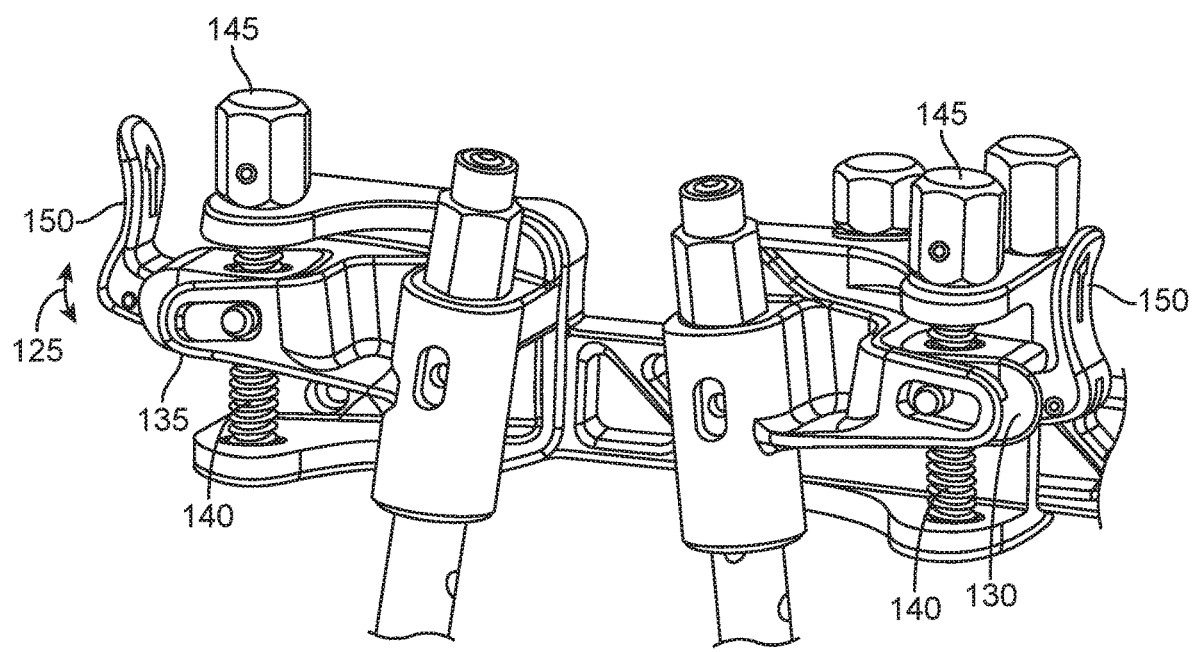
FIG. 3 is a perspective view showing an upper portion of the minimally invasive surgery (MIS) multi-level compressor/distractor instrument of FIGS. 1 and 2.
Figure 4:
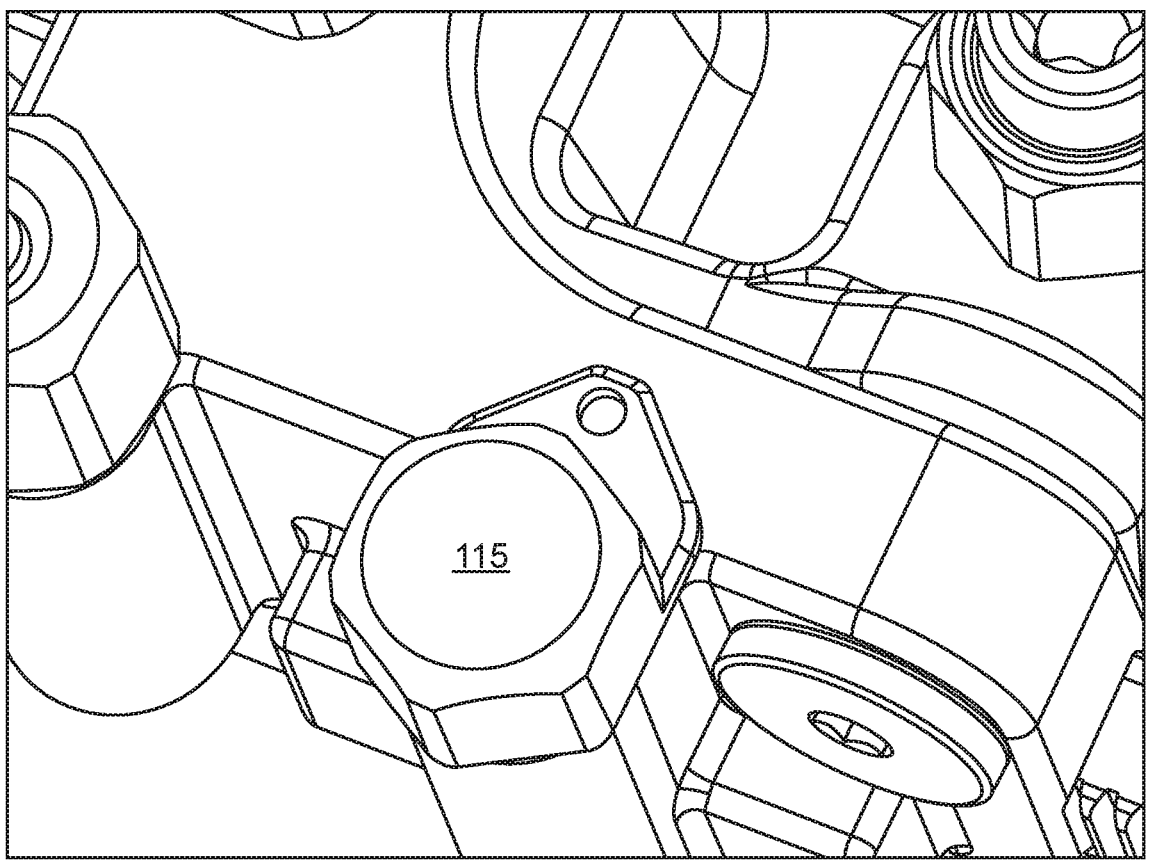
FIG. 4 is a perspective view showing ratchet settings.
Figure 5:
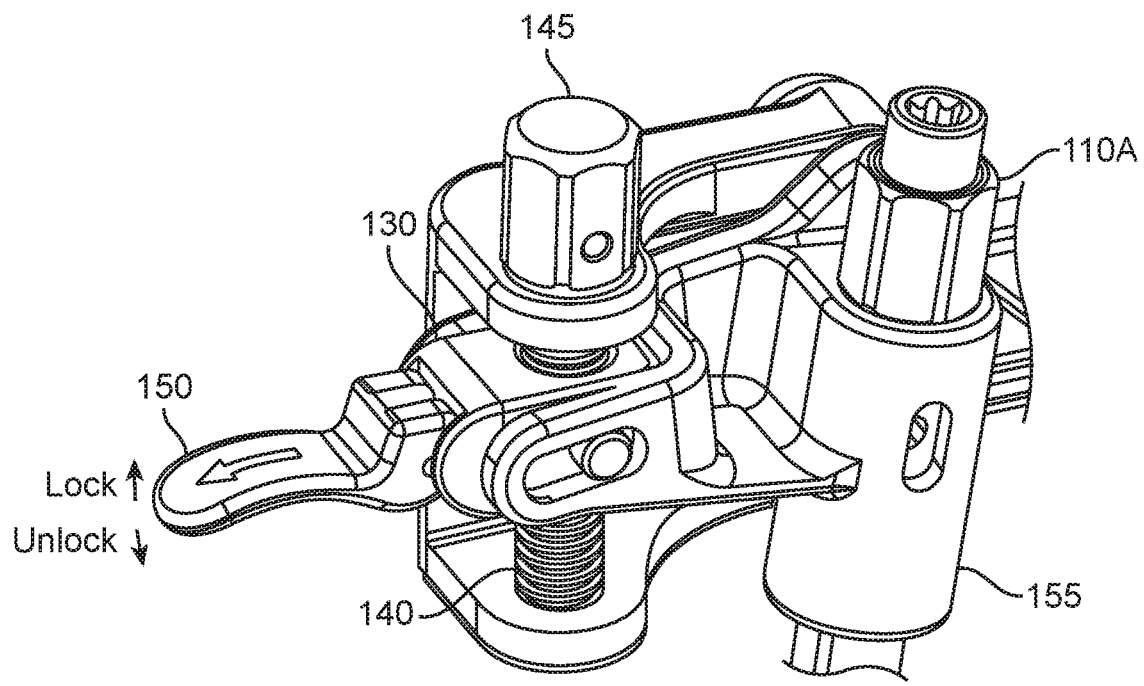
FIGS. 5 and 6 show details of the left and right pivoting arm and locking mechanism
Figure 6:
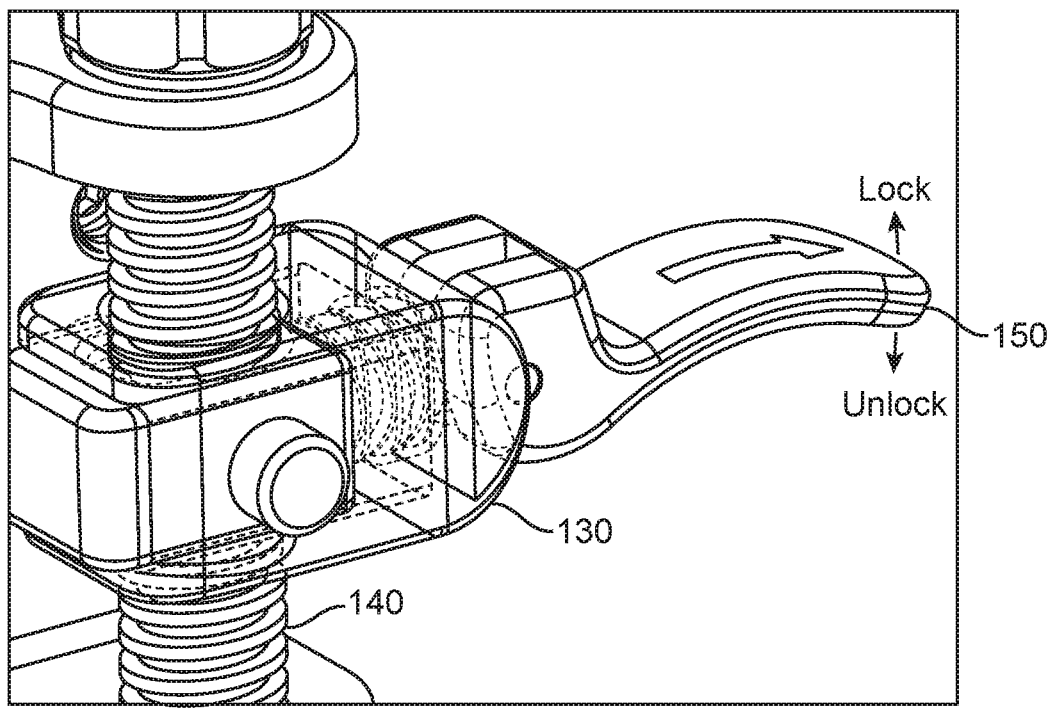
Figure 7:
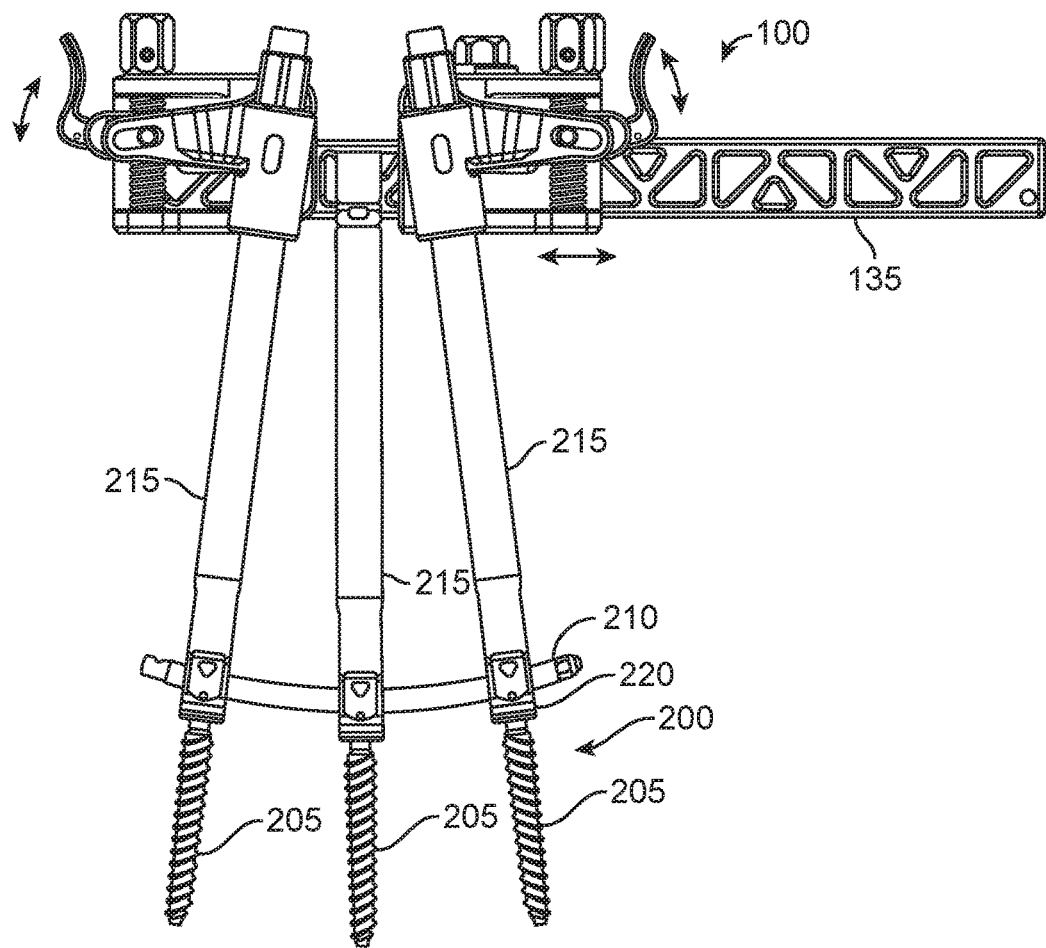
FIGS. 7-11 are views showing the operation of the minimally invasive surgery (MIS) multi-level compressor/distractor instrument.
Figure 8:
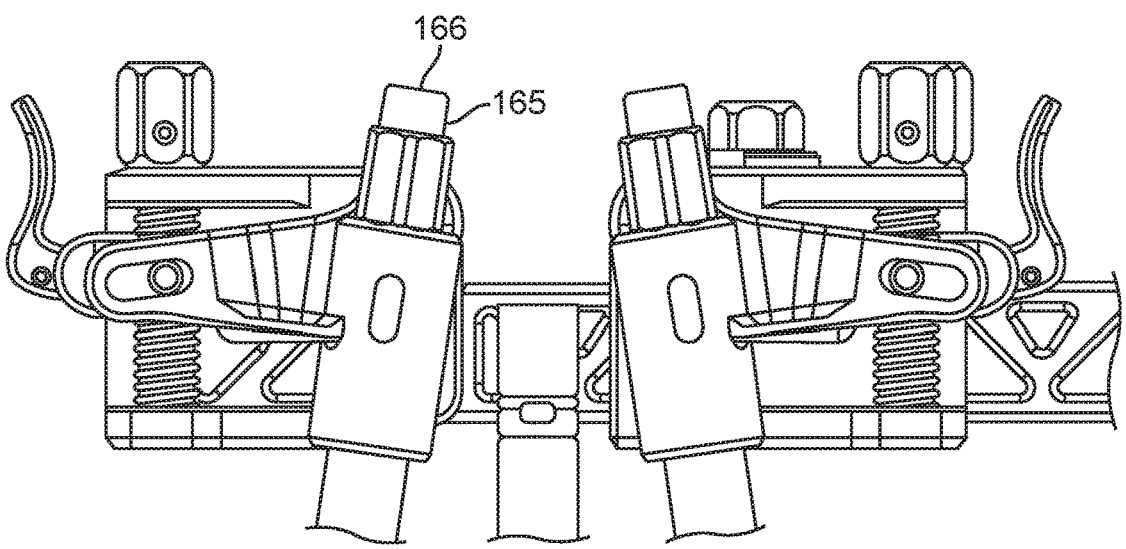

FIGS. 1 and 2 show one embodiment of a minimally invasive surgery (MIS) multi-level compressor/distractor instrument 100 comprising a multi-level compressor/distractor device 105 and compressor/distractor support tubes 110a, 110b. used with screw extender system 200 for multilevel compression and distraction of vertebrae in two directions. First, compression and distraction is provided in a linear direction 115 by way of a ratcheting 120 rack and pinion system, and second, compression and distraction is achieved by inducing lordosis or kyphosis 125 by way of two pivoting arms 130.

The rack and pinion system of the multi-level compressor/distractor device 105 includes a ratchet 120 coupled to a slide rail 135. In some embodiments, the ratchet 120 may be positioned in one of three positions: compress 120*a*, distract 120*b* or neutral 120*c* position. In the compress or distract positions 120*a*, 120*b*, when the ratchet 120 is operated, the slide rail 135 pivoting arms 130 move linearly 115 to compress or distract. When the ratchet is set to neutral position 120*c*, the slide rail 135 to move freely for ease in setting up spinal construct.

The multi-level compressor/distractor device 105 also includes two pivoting arms 130 controlled by a threaded shaft 140 and nut 145. As the nut 145 is turned, the pivoting arms 130 travel up or down the threaded shaft 130 pivoting the arm 130 for lordosis or kyphosis 125 adjustment. A thread release cam 150 may also be provided to decouple the pivot arms 130 from the threaded shaft 140 to allow the pivot arms 130 to slide freely in setting up the spinal construct. In some embodiments, the release can 150 may be spring loaded for locking and releasing.

The multi-level compressor/distractor device 105 also tube engagement arms 155*a*, 155*b* having an opening 156 configured to receive the compressor/distractor support tubes 110*a*, 110*b* and pedicle screw extenders 215 (see FIGS. 7-11). The multi-level compressor/distractor device 105 may be configured to include a third arm (not shown) in other embodiments for multilevel compression/distraction procedures. The multi-level compressor/distractor device 105 may be configured for single level compression/distraction procedures if desired.

In the embodiments shown, the tube engagement arms 155 are substantially perpendicularly protrude to the pivoting arms 130. The ratchet 120 is positioned on the opposite side where the tube engagement arms 155 are positioned. The ratchet 120 is configured to cause movement of the tube engagement arms 155 to and from each other. The ratchet 120 can be configured to use any ratcheting mechanism. In some embodiments, the ratchet 120 can be configured to have a nut portion to allow the use of a socket or wrench. The tube engagement arms 155 further include respective inner openings 156 configured to accommodate placement of the compressor/distractor support tubes 110*a*, 110*b* and screw extenders 215. The movement of the ratchet 145 changes the distance between the tube engagement arms 155 for linear compression or distraction 115, and the movement of the pivot arms 130 change the angle 125 of the tube engagement arms 155 to allow tilting of the screw extenders 215 for lordosis or kyphosis compression or distraction motions.

The compressor/distractor support tubes 110*a*, 110*b* include a tubular body 160 having a central lumen housing a screw driving shaft 165. The body 160 is configured to fit within the openings 156 on the tube engagement arms 155*a*, 155*b*. The tubular body 160 further includes a proximal cap 170 having a male threaded portion 175 configured to engage female threads on the pedicle screw extenders 215. The compressor/distractor support tubes 110*a*, 110*b* are also configured to fit within screw extensions 215 and provide bending support screw extensions 215 during compression or distractor manipulation.

The MIS compressor/distractor support tubes 110*a*, 110*b* provide internal set screw engagement for threaded reduction capabilities while also providing bending support during compression or distraction manipulation. Threaded reduction is performed by engaging the MIS Compressor/Distractor Support Tubes at the proximal end with a driver.

FIGS. 7-11 show the compressor/distractor device 105 in use with a multi-level spinal fixation system 200 having pedicle screws 205 attached to two or more vertebrae (not shown) coupled to a fixation rod 210. Screw extenders 215 are removably attached to the pedicle screws 205 to assist in assembling and adjusting the spinal fixation system 200. The screw extenders 215 include a tubular body with a central opening or lumen extending through the body. The proximal end of the screw extenders 215 includes female threads. The compressor/distractor support tubes 110*a*, 110*b* are sized to fit within the lumen and the male threads 175 engage the female threads to hold the support tubes in place and provide bending support of the screw extenders 215 during compression or distractor manipulation of the compressor/distractor device 105.

The pedicle screws 205 include a body member or head 220 that includes a U-shaped channel or slot 225 to accept the fixation rod 210. A set screw 230 is used to threadably engage the body member 220 of the screw assembly to secure the fixation rod 210 within the body member 220.

The proximal end 166 of the screw driving shaft 165 is configured to engage a screw driver or other tool 300. The distal end of the screw driving shaft 167 is configured to engage and rotate the set screw 230 to reduce and seat the fixation rod 210 in the U-shaped channel or slot 225 of the screw head 220.

With this design, the compressor/distractor support tubes 110*a*, 110*b* provide internal set screw 230 engagement for threaded reduction capabilities of the fixation rod 210, while also providing bending support of the screw extensions 215 during compression or distractor manipulation of the compressor/distractor device 105.

In operation, the compressor/distractor support tube 110 is slide into the top of the openings 156 to the support tube engagement arms 155*a*, 155*b* of the compressor/distractor 105 and the screw extenders 215 are slid into the bottom of the openings 156. The male threads 175 of the compressor/distractor support tubes 110 are then coupled to the female threads of the screw extenders 215. The distal end 167 of the screw driving shaft 165 are configured to engaged with the set screws 225.

The left and right pivot arms 130 of the compressor/distractor device 105 are then moved along the rail 135 for linear compression or distraction of the screw extenders 215, and/or the pivot arms 130 are rotated for lordosis or kyphosis compression or distraction of the screw extenders 215, with the compressor/distractor support tubes 110 providing support for the screw extenders 215.

Figure 9:
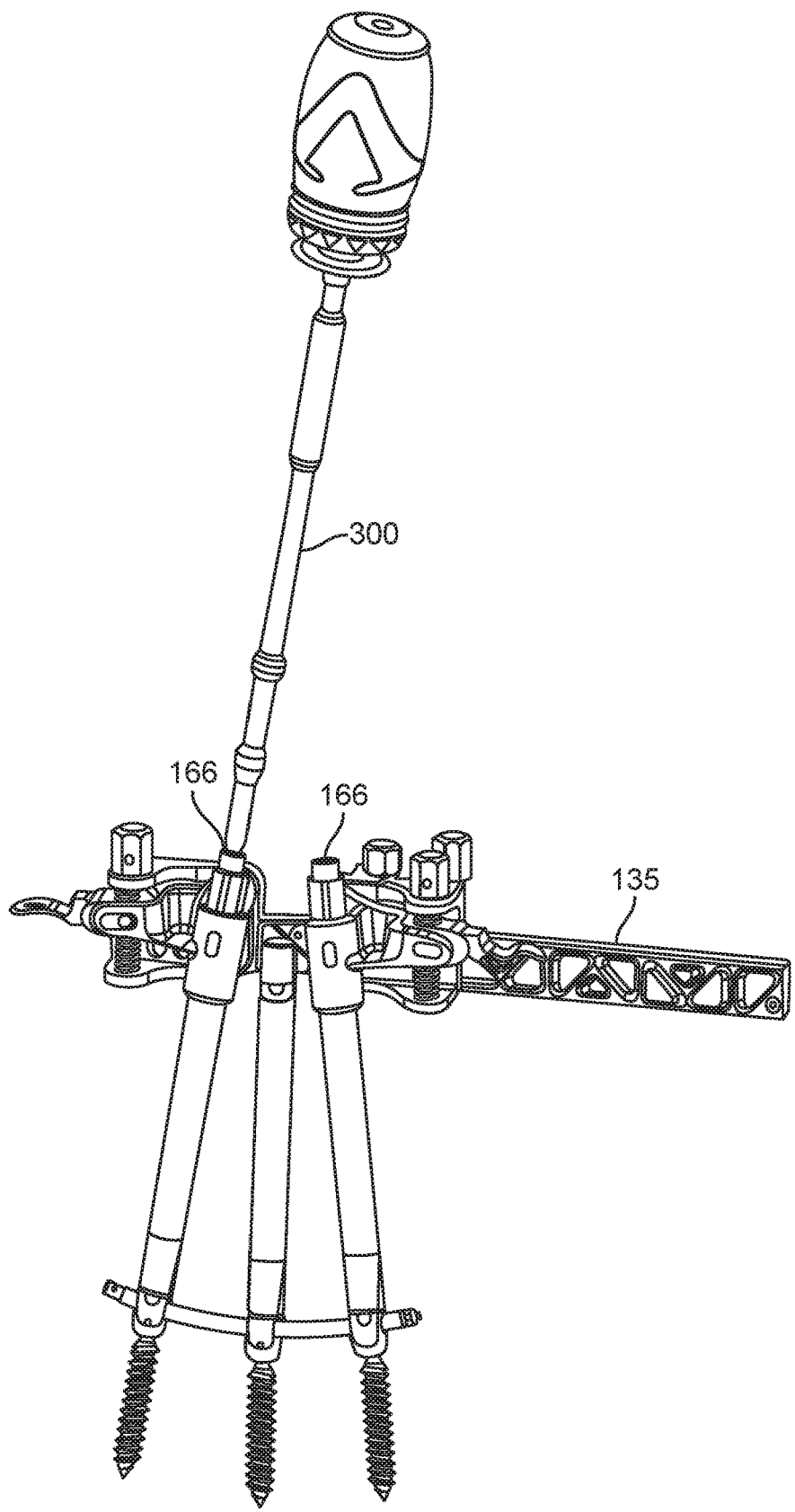

FIG. 9 shows a screwdriver or other instrument 300 coupled to the proximal end 166 of the first screw driving shaft 165 to rotate the set screw 230 to reduce the fixation rod 210 into the u-shaped channel 225 of the body member 220 and lock the fixation rod in place.

Figure 10:
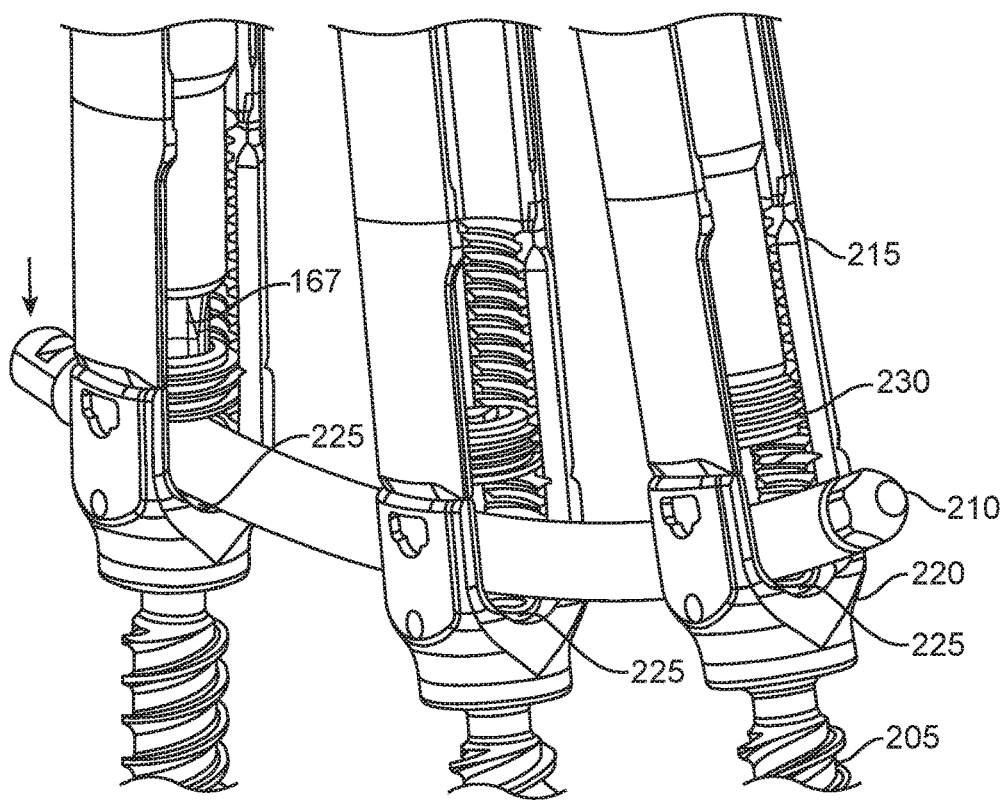

FIG. 10 shows the fixation rod reduction on the left tube 215. The inside lumen of the left screw extension 215 and screw head 220 include female threads configured to engage male threads of the set screw 230. For rod reduction, the distal end 167 rotates the set screw 230 down the threads, which pushes the fixation rod 210 downward D into the U-shaped channel 225.

Figure 11:
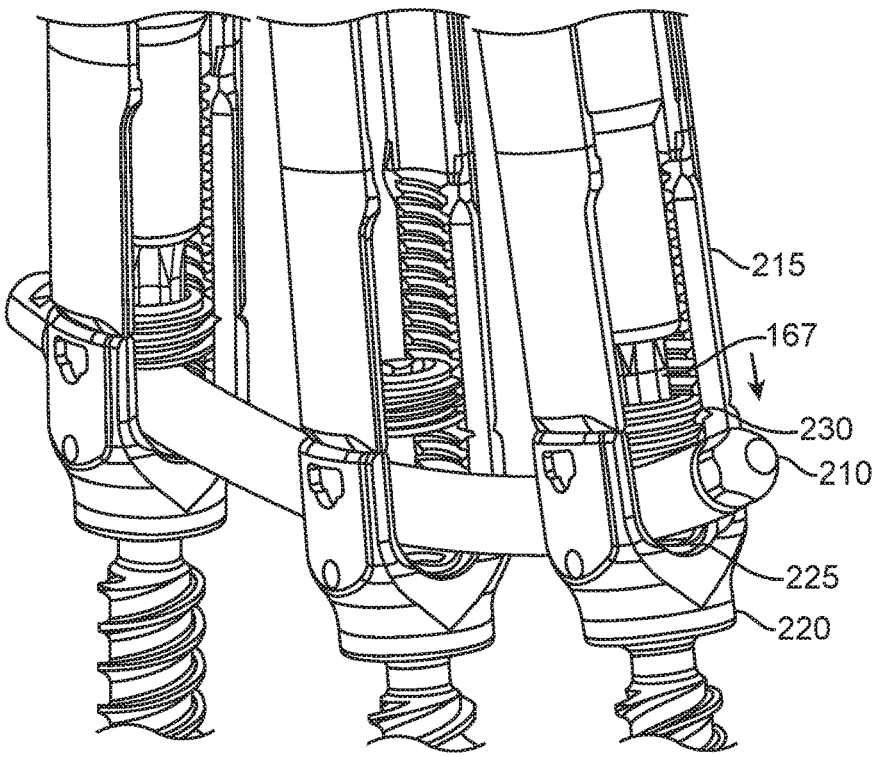

FIG. 11 shows the fixation rod reduction on the right tube. The inside lumen of the right screw extension 215 and screw head 220 include female threads configured to engage male threads of the set screw 230. The distal end 167 rotates the set screw 230 down the threads, which pushes the fixation rod 210 downward D into the U-shaped channel 225.

The screw driver 300 is then inserted into the center screw extension and rotates the set screw 230 to engage the fixation rod 210 and secure it within the U-shaped channel 225 of the center screw head. The compressor/distractor instrument 100 may now be removed.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A compressor/distractor instrument comprising:
a compressor/distractor device having:
a ratcheting mechanism having a ratchet configured to move in a linear direction on a slide rail and
right and left pivoting arms coupled to screw extenders, the left pivoting arm being coupled to the slide rail and the right pivoting arm being coupled to the ratchet, each pivoting arm being coupled to a threaded shaft and nut, the pivoting arms are configured to move in an angular direction to change an angle between the pivoting arms to allow tilting of the screw extenders for lordosis or kyphosis compression or distraction motion; and
compressor/distractor support tubes coupled to the right and left pivoting arms configured to fit within the screw extenders to provide bending support during compression or distraction of vertebrae;
wherein the compressor/distractor device and the compressor/distractor support tubes used with a screw extender system for movement of vertebrae in two directions, the ratchet provides movement on the slide rail in the linear direction for compression or distraction of the vertebrae, and the right and left pivoting arms travel up or down the threaded shafts by rotating the nuts to change the angular direction for lordosis or kyphosis of the vertebrae.

2. The instrument of claim 1, wherein the compressor/distractor support tubes include a tubular body with a central lumen sized to fit within a pedicle screw extender of the screw extender system and provide bending support to the pedicle screw extenders.

3. The instrument of claim 1, wherein the ratchet and the left pivoting arm are configured to move linearly on the slide rail to change a distance between the right and left pivoting arms.

4. The instrument of claim 1, wherein the ratchet may be positioned in three positions: compress, distract, or neutral, wherein the neutral position allows the ratchet to move freely on the slide rail for ease in setting up the system.

5. The instrument of claim 1, wherein the compressor/distractor support tubes further comprising a screw driver shaft configured to fit within a central lumen of the support tubes, the screw driver shaft-having a proximal end configured to engage a screw driver and a distal end configured to engage a set screw.

6. The instrument of claim 1, wherein the pivoting arms includes a thread release cam configured to decouple the pivoting arm from the threaded shaft to allow the pivoting arms to move freely for ease in setting up the system.

* * * * *